United States Patent [19]

Mayra-Makinen

[11] Patent Number: 4,929,546
[45] Date of Patent: May 29, 1990

[54] TEST SET AND A PROCESS FOR THE DETERMINATION OF ANTIBIOTICS IN MILK AND A NOVEL STREPTOCOCCUS THERMOPHILUS STRAIN TO BE USED THEREIN

[75] Inventor: Annika Mayra-Makinen, Helsinki, Finland

[73] Assignee: Valio Meijerien Keskusosuusliike, Helsinki, Finland

[21] Appl. No.: 178,257

[22] Filed: Apr. 6, 1988

[30] Foreign Application Priority Data

Apr. 7, 1987 [FI] Finland ............................ 871512

[51] Int. Cl.$^5$ ............................................. C12Q 1/02
[52] U.S. Cl. ........................................ 435/29; 435/32; 435/33; 435/36; 435/253.4; 426/34; 426/42; 426/43; 426/61
[58] Field of Search ................ 435/29, 885, 32, 810, 435/33, 253.4, 885, 36; 436/61, 34, 42, 43

[56] References Cited

U.S. PATENT DOCUMENTS 4,235,964 11/1980 Bochner ............................... 435/34
4,615,978 10/1986 Sandine et al. ...................... 435/253

OTHER PUBLICATIONS

Jacobs et al, "Simple Rapid Test for Detection of Antibiotic Residues in Milk", 1972, Intervet. Int. N.V., Boxmeer, Neth, Tijdschr. Diergeneesk., 97(9), 548, 549–50.

Primary Examiner—Robert J. Warden
Assistant Examiner—Laurie A. Scheiner
Attorney, Agent, or Firm—Kenyon & Kenyon

[57] ABSTRACT

A test set comprising a purified culture of *Streptococcus thermophilus* T101 concentrate and a water-based protective agent in dilution ratio of about 4 to $5 \times 10^{-2}$. The test set may also advantageously comprise an indicator. The test method includes the steps of incubating the test set and evaluating the color. The present invention also comprises a purified culture of *Streptococcus thermophilus* T101 strain.

25 Claims, No Drawings

TEST SET AND A PROCESS FOR THE DETERMINATION OF ANTIBIOTICS IN MILK AND A NOVEL STREPTOCOCCUS THERMOPHILUS STRAIN TO BE USED THEREIN

The present invention is directed to a test set suitable for the determination of antibiotics in milk. The invention is also directed to a novel *Streptococcus thermophilus* strain to be used in the test set and a process for the determination of antibiotics in milk utilizing said test set.

BACKGROUND

In many situations it is of vital importance to be able to detect the presence of small amounts of antibiotics. This is the case in food industries, for instance, where the increased use of antibiotics and chemotherapeutic substances in the treatment of animals has created a need for a simple, reliable and sensitive process of determination. Since antibiotics are used also in the treatment of dairy cows and since antibiotic residues in milk may both cause health hazards and be disadvantageous for food technological reasons, it is especially important to develop processes suitable for an accurate and rapid screening of milk.

Antibiotic residues in milk are generally detected by microbiological processes which utilize the fact that bacteria are able to produce acid, reduce colours and produce growth on an agar medium. These processes are based on the bactericidal, inhibitory and morphological effect of antibiotics on certain microorganisms.

The Thermocult disk technique is an agar diffusion technique which is widely used in Finland and accepted as an official antibiotic determination procedure. In this technique the test organism is *B. stearothermophilus* var. *calidolactis*. It has been developed on the basis of an IDF standard process (IDF 1970. Detection of Penicillin in Milk by a Disk Assay Technique. International Standard FIL-IDF 57. Brussels).

A process of corresponding sensitivity is disclosed by Van OS et al., Diffusion Test for the Determination of Antibiotic Residues in Milk. Neth. Milk and Dairy J. 29 (1975) 16. The Delvotest process also uses *B. stearothermophilus* var. calidolactis as the test organism. A sample (0.1 ml) is pipetted on agar contained in an ampoule and a tablet containing nutrients and a pH indicator is added to the ampoule. The process is based on the acid producing capability of the test organism. The ampoules are incubated at 64° C. for 2 5 hours. The evaluation is based on the colour change of the agar layer.

Standard techniques further include the Intertest (BCP-Test). The test microbe used in this process is *Str. thermophilus*. A test tablet containing a lyophilized culture of the test microbe, nutrients, and a pH indicator (bromocresol purple) is added to a milk sample. The incubation time is 4 hours at 45° C. If the sample does not contain any antibiotic, the colour of the solution turns from blue to green and further to yellow. The amount of the antibiotic can be determined to some extent on the basis of the colour by comparing to a colour map (THOROGOOD et al., An Evaluation on the Charm Test - A Rapid Method for the Detection of Penicillin in milk. J. Dairy Research 50 (1983) 185).

A drawback of these processes is their insufficient sensitivity in view of the needs of milk technology.

The determination of antibiotic residues in milk by means of chemical or physico-chemical processes is considerably less common than the use of microbiological processes. Colorimetric and chromatographic processes require skilled labour and often a complicated and expensive analyzing equipment. The processes are seldom suitable for routine analyses.

The Charm test (CHARM, S.E., A 15-minute Assay for Penicillin and other Antibiotics. Cultured Dairy Products J. 14 (1979) 24) is based on the detection of radioactivity. A lyophilized culture of *B. stearothermophilus* culture and lyophilized $^{14}C$-labelled penicillin are added to a sample. The amount of $^{14}C$ contained in the bacterium cells is detected by a Geiger counter; the lower the penicillin concentration of the sample, the higher is the reading of the Geiger counter. The detection time is only 15 minutes and the sensitivity of the process is 0.005 I.U. of penicillin per ml. This process is also not particularly suitable for routine use since it is expensive and complicated and requires skilled persons and expensive equipment to be carried out.

Thus there is still a practical need for a sensitive process which has as broad-spectrum as possible. The process should advantageously be simple and should be capable of being carried out with equipment ready for use, whereby the test does not require specially skilled persons, but can be readily carried out, for example, on a farm.

BRIEF DESCRIPTION

These advantages are obtained by the present invention which comprises a test set comprising a purified culture of *Streptococcus thermophilus* T101 concentrate and a water-based protective agent in dilution ratio of about 4 to $5 \times 10^{-2}$. The test set may also advantageously comprise an indicator. If the test set does not comprise an indicator, an indicator is added. The test includes the steps of incubating the test set and the sample at about 38° to 42° C. for about 4 hours; and evaluating the colour. The present invention also comprises a purified culture of *Streptococcus thermophilus* T101 strain.

DETAILED DESCRIPTION

The present invention comprises a novel purified culture *Streptococcus thermophilus* T101 strain, which has been isolated at the Lammi creamery of Valio. The strain has been deposited at the Deutsche Sammlung von Mikroorganismen, Griesebachstrasse 8, 3400 Gottingen, Federal Republic of Germany under the deposit number DSM 4022 on Mar. 3, 1987, and it possesses the following properties:

gram positive,
forms long coccus chains
growing temperature:
   growth at 50° C.
   no growth at 10° C.
salt resistance
   growth at a NaCl concentration of 2% by wgt.
   no growth at a NaCl concentration of 6.5%,
titrated acidity 25° to 29° SH (Soxhlet-Henkell) after
   7-hour incubation at 42° C. (sterilized 10% milk powder milk)
lactic acid %: 0.8% by volume (incubated 2 days at 42° C., from milk powder milk)
   fermentates lactose, saccharose and glucose.

The Applicant has provided that:

(a) access to the culture will be available during pendency of the patent application to one determined by the Commissioner to be entitled thereto under 37 CFR 1.14 and 35 U.S.C. 122;

(b) all restrictions on the availability to the public of the culture so deposited will be irrevocably removed upon the granting of the patent; and (c) permanent availability of the culture to the public through the Deutsche Sammlung von Mikroorganismen is assured.

Judging from the values given in the prior art, the novel microorganism strain is clearly more sensitive than known *Streptococcus thermophilus* strains, especially to penicillin and oxytetracycline.

The test is preferably prepared in the following way:

The microorganism strain is grown in a fermentor at a pH of about 6.2 to 6.5 and at about 38° to 42° C. in a culture medium based on whey permeate. The growth is observed and the growth is arrested at the end of the logarithmic growth phase whereafter the culture broth is concentrated by filtrating to about a 20-fold concentration. The concentration is measured in a dilution ratio of about 4 to $5 \times 10^{-2}$, preferably about $5 \times 10^{-2}$, into a protective agent. The protective agent may consist of water-based protective agents used in the preparation of lyophilized microbe preparations. Preferably the protective agent is an aqueous solution comprising about 1.1% of sodium glutamate, about 1.1% of ascorbic acid, and optionally about 7% of lactose, and the pH of which is about 6.5. The indicator can be added to the protective agent or it can be added to the test set in connection with the determination. The indicator is a conventional indicator as is known in the art e.g. an acid-base indicator, such as bromocresol purple. The concentrate is measured into a vessel which may be a conventional ampoule, a sealable test tube, a sample bottle, or the like. The vessel is rapidly cooled for example in a carbonic acid-sulphite alcohol bath, whereafter it is lyophilized and stored under vacuum. The finished test set contains about 1 to $2 \times 10^6$ bacteria per ml.

The antibiotic determination is carried out by adding a liquid sample and, when an indicator has not already been added to the test set, an indicator to the test set. The test set and the sample are then incubated and the colour changes are observed. If the sample contains antibiotics, the microorganisms in the test set are not able to grow and the colour does not change. On the other hand, if the sample does not contain antibiotics, the microorganisms grow and induce a colour change while growing.

The sensitivity of the process according to the invention was compared with the corresponding commercial THERMOCULT (Orion Diagnostica) and DELVOTEST P (Gist-Brocades) techniques and the CHARM II technique. The sample consisted of milk preheated at 95° C. for 5 minutes and the determinations were carried out according to the instructions given by the manufacturers. The results are presented in Table 1, from which further appears the data given by the manufacturer Intervet concerning the INTERTEST. The results show that the process according to the invention is more sensitive than the other processes and detects clearly the presence of all types of antibiotics/combinations.

TABLE

Experimentally determined antibiotic sensitivities (µg/ml) of the tested determination processes

| ANTIBIOTIC | PROCESS ACCORDING TO THE INVENTION A | PROCESS ACCORDING TO THE INVENTION B | THERMOCULT own determination | THERMOCULT (S & S) (a) | DELVOTEST P own determination | DELVOTEST P (S & S) (a) | IN-TEREST (b) | CHARM TEST II |
|---|---|---|---|---|---|---|---|---|
| PENICILLIN | 0.001–0.002 I.U. | 0.001–0.002 I.U. | 0.006–0.0075 | 0.005–0.0075 | 0.0025 | 0.0025 | 0.005 | 0.003 |
| STREPTOMYCIN | 1.25 | 0.25–0.4 | 5.0 | 2.5–5.0 | 5.0 | 2.5–5.0 | 5.0 | 0.1 |
| TETRACYCLINE | 0.05–0.1 | 0.05 | 0.2(c) | 0.1 | 0.2 | 0.1 | 0.5 | 0.2 |
| OXYTETRACYCLINE | 0.1 | 0.05 | 0.2(c) | 0.1 | 0.2 | 0.1 | 0.2 | |
| AMPICILLIN | 0.01 | 0.003 | 0.01(c) | 0.005 | 0.01(c) | 0.005 | 0.005 | |
| ERYTHROMYCIN | 0.01–0.05 | 0.01 | 0.1(c) | 0.5–0.75 | 0.1(c) | 0.75–1.0 | 0.1 | 0.01 |
| CHLORAMPHENICOL | 0.1–0.5 | 0.1 | 1.0(c) | 7.5 | 1.0(c) | 7.5–10.0 | 1.0 | 0.05 |
| NEOMYCIN | 0.5 | 0.1–0.2 | 0.5 | 1.0 | 1.0 | 0.5 | 20.0 | |
| STREPTOMAX (penicillin + streptom.) | 0.004 I.U. PEN + 0.001 µg/ml STREPTOM. | | 0.01 I.U. PEN + 0.008 µg/ml STREPTOM. | | | | | |
| MASTALONE (oxytetracycline + the others) | 0.1 | 0.05 | 0.2(c) | | | | | |

A indicator added in connection with the test (duration of the test 4 hours)
B indicator added before freeze drying (duration of the test 5 hours)
(a) Sandstrom & Sivela, 1984, Karjantuote 4
(b) concentrations given by the manufacturers
(c) could not be determined

EXAMPLE 1

Preparation of the test:

Bacteria of the *Streptococcus thermophilus* T101 strain are inoculated in a culture medium having the following composition:

5% by wgt. of whey permeate powder
1.5% by wgt. of casein hydrolysate
0.5% by wgt. of tryptone
1% by wgt. of yeast extract The culture medium is sterilized at 12° C. for 15 to 20 minutes, and its pH is 6.4 after the sterilization.

The test strain is grown in a fermentor at a pH of about 6.2 and at about 42° C., and the growth is monitored by observing the turbidity of the culture broth. At the end of the logarithmic growth phase the growth is arrested and the culture broth is concentrated by filtrating using a Millipore Pellicon filtration unit (0.45 m) to a 20-fold concentration, whereby the bacterium concentration of the concentrate is about $2 \times 10^9$ bacteria per ml. The concentrate is washed with a small amount of protective agent, and about 5 ml. is added to 100 ml. of protective agent, whereto is possibly also added 1 ml of bromocresol purple colour (a 0.8% solution). The bacterium concentration of the solution so obtained is about $1\times10^8$ bacteria per ml. 1 ml of the solution is added to a conventional 10 ml ampoule which withstands drying and can be closed by vacuum. The ampoule is cooled rapidly (20 to 60 s) in a $-60°$ C. carbonic acid-sulphite alcohol bath, whereafter it is freeze dried and vacuum closed for storage. The ampoule thus prepared contains 1 to $2\times10^6$ bacteria per ml.

EXAMPLE 2

Determination of antibiotics in a milk sample:

Raw milk is heated at 95° C. for 5 minutes. 2 ml of milk and possible 20 μl of a colour indicator are added to a test set prepared according to Example 1. The test set is incubated for about 4 hours at about 42° C. and the colour is evaluated. Milk prepared from sour milk powder and heated at 95° C. for 5 minutes is used as a control. If the milk contains antibiotics, the colour turns blue. Yellow indicates a negative result.

The examples were carried out using the protective agent mentioned on page 5 and both in the presence and absence of the optional 7% lactose. The results obtained are the same, but lactose has an advantageous effect on the appearance and properties of the lyofilized product. Without lactose the freeze-dried product easily crumbles; with lactose a perfect pellet which retains its integrity is obtained.

I claim:

1. A test set suitable for the determination of the presence of antibiotics in milk comprising a *Streptococcus thermophilus* T101 DSM 4022 concentrate and a water-based protective agent.

2. A test set according to claim 1 wherein said concentrate is in a dilution ratio of about 4 to $5\times10^{-2}$.

3. A test set according to claim 1 wherein said protective agent comprises an aqueous solution comprising about 1.1% by wgt. sodium glutamate and about 1.1% by wgt. ascorbic acid.

4. A test set according to claim 3 wherein said protective agent further comprises about 7% by wgt. lactose.

5. A test set according to claim 3 wherein said protective agent has a pH of about 6.5.

6. A test set according to claim 1 wherein said test set further comprises an indicator.

7. A test set according to claim 6 wherein said indicator is bromocresol purple.

8. The microorganism comprising a purified culture of *Streptococcus thermophilus* T101, DSM 4022.

9. A process for determining the presence of antibiotics in milk comprising the steps of:
(a) adding a sample of milk to a test set comprising a *Streptococcus thermophilus* T101, DSM 4022 concentrate and a water-based protective agent,
(b) adding an indicator to said test set,
(c) incubating the test set and the sample, and (d) evaluating the color of the test set, wherein a color change is an indication of the presence of an antibiotic in the milk sample.

10. A process according to claim 9 wherein said test set comprises *Streptococcus thermophilus* in a dilution ratio of from 4 to $5\times10^{-2}$.

11. A process according to claim 9 wherein said sample is incubated at temperature of about 38–42 degrees C.

12. A process according to claim 9 wherein said sample is incubated for about four hours.

13. A method for preparing a test set suitable for the determination of the presence of antibiotics in milk comprising the steps of:
(a) growing *Streptococcus thermophilus* T101 DSM 4022 in a culture medium,
(b) concentrating said *Streptococcus Thermophilus* T101 growth,
(c) adding said concentrate to a protective agent, and
(d) rapidly cooling the concentrate and protective agent solution.

14. A method according to claim 13 wherein said culture medium comprises:
(a) about 5% by wgt. whey permeate powder,
(b) about 1.5% by wgt. casein hydrolysate,
(c) about 0.5% by wgt. tryptone, and
(d) about 1% by wgt. yeast extract.

15. A method according to claim 13 wherein said *Streptococcus thermophilus* T101 is grown at a pH of about 6.2.

16. A method according to claim 13 wherein said *Streptococcus thermophilus* T101 is grown at a temperature of about 42 degrees C.

17. A method according to claim 13 wherein said growth is concentrated to a bacterium concentration of about $2\times10^9$ bacteria per ml.

18. A method according to claim 13 wherein an indicator is added to said concentrate and protective agent solution prior to cooling.

19. A method according to claim 18 wherein said indicator is a 0.8% solution of bromocresol purple.

20. A method according to claim 13 wherein said concentrate and protective agent solution is cooled in a carbonic acid-sulphite alcohol bath.

21. A method according to claim 20 further comprising the steps of freeze drying and vacuum sealing said solution.

22. A process for determining the presence of an antibiotic in milk comprising the steps of:
(a) adding a sample of milk to a test set comprising a *Streptococcus thermophilus* T101, DSM 4022 concentrate, a water-based protective agent and an indicator,
(b) incubating the test set and the sample, and
(c) evaluating the color of the test set, wherein a color change is an indication of the presence of an antibiotic in the milk sample.

23. A process according to claim 22, wherein said test set comprises *Streptococcus thermophilus* T101, DSM 4022 in a dilution ratio of from 4 to $5\times10^{-2}$.

24. A process according to claim 22, wherein said sample is incubated at a temperature of about 38–42 degrees C.

25. A process according to claim 22, wherein said sample is incubated for about 4 hours.

* * * * *